(12) United States Patent
Sandler et al.

(10) Patent No.: US 7,733,485 B2
(45) Date of Patent: Jun. 8, 2010

(54) MEASURING METHOD AND SYSTEM FOR MEASURING PARTICLE SIZE AND SHAPE OF POWDERY OR GRAIN LIKE PARTICLES

(75) Inventors: Niklas Sandler, Helsinki (FI); Osmo Antikainen, Helsinki (FI); Jouko Yliruusi, Vantaa (FI)

(73) Assignee: Intelligent Pharmaceutics Ltd Oy, Helsinki (FI)

( * ) Notice: Subject to any disclaimer, the term of this patent is extended or adjusted under 35 U.S.C. 154(b) by 153 days.

(21) Appl. No.: 11/919,831

(22) PCT Filed: Apr. 27, 2006

(86) PCT No.: PCT/FI2006/000137

§ 371 (c)(1),
(2), (4) Date: Mar. 6, 2008

(87) PCT Pub. No.: WO2006/117429

PCT Pub. Date: Nov. 9, 2006

(65) Prior Publication Data

US 2009/0091755 A1    Apr. 9, 2009

(30) Foreign Application Priority Data

May 2, 2005    (FI)    ................................. 20050470

(51) Int. Cl.
*G01N 15/02*    (2006.01)
(52) U.S. Cl. ..................................................... 356/335
(58) Field of Classification Search .................. 356/335; 382/108
See application file for complete search history.

(56) References Cited

U.S. PATENT DOCUMENTS

| 4,040,747 | A | 8/1977 | Webster |
| 5,239,358 | A | 8/1993 | Tokoyama et al. |
| 6,122,042 | A | 9/2000 | Wunderman et al. |
| 7,113,265 | B1* | 9/2006 | Sarrazin et al. ............... 356/73 |
| 2003/0048927 | A1* | 3/2003 | Sato et al. .................... 382/110 |
| 2005/0090011 | A1 | 4/2005 | Du Plessis |

FOREIGN PATENT DOCUMENTS

| JP | 10-10033 | 6/1996 |
| WO | WO 98/30886 A1 | 7/1998 |

\* cited by examiner

*Primary Examiner*—Roy Punnoose
(74) *Attorney, Agent, or Firm*—Birch, Stewart, Kolasch & Birch, LLP

(57) ABSTRACT

The invention relates to a measuring method for measuring the properties of a powder or granular sample (1) from the surface information of the sample. According to the method the sample is leveled for the measurement, at least one image of the surface of the sample (1) is taken and the properties, such as the grain-size distribution, of the sample (1) are determined by processing the information material by calculation. According to the invention, the sample (1) is made to be supported on a transparent sample plate (2, 13, 14, 15) and an image is taken through this sample plate (2, 13, 14, 15).

16 Claims, 5 Drawing Sheets

Figure 1:
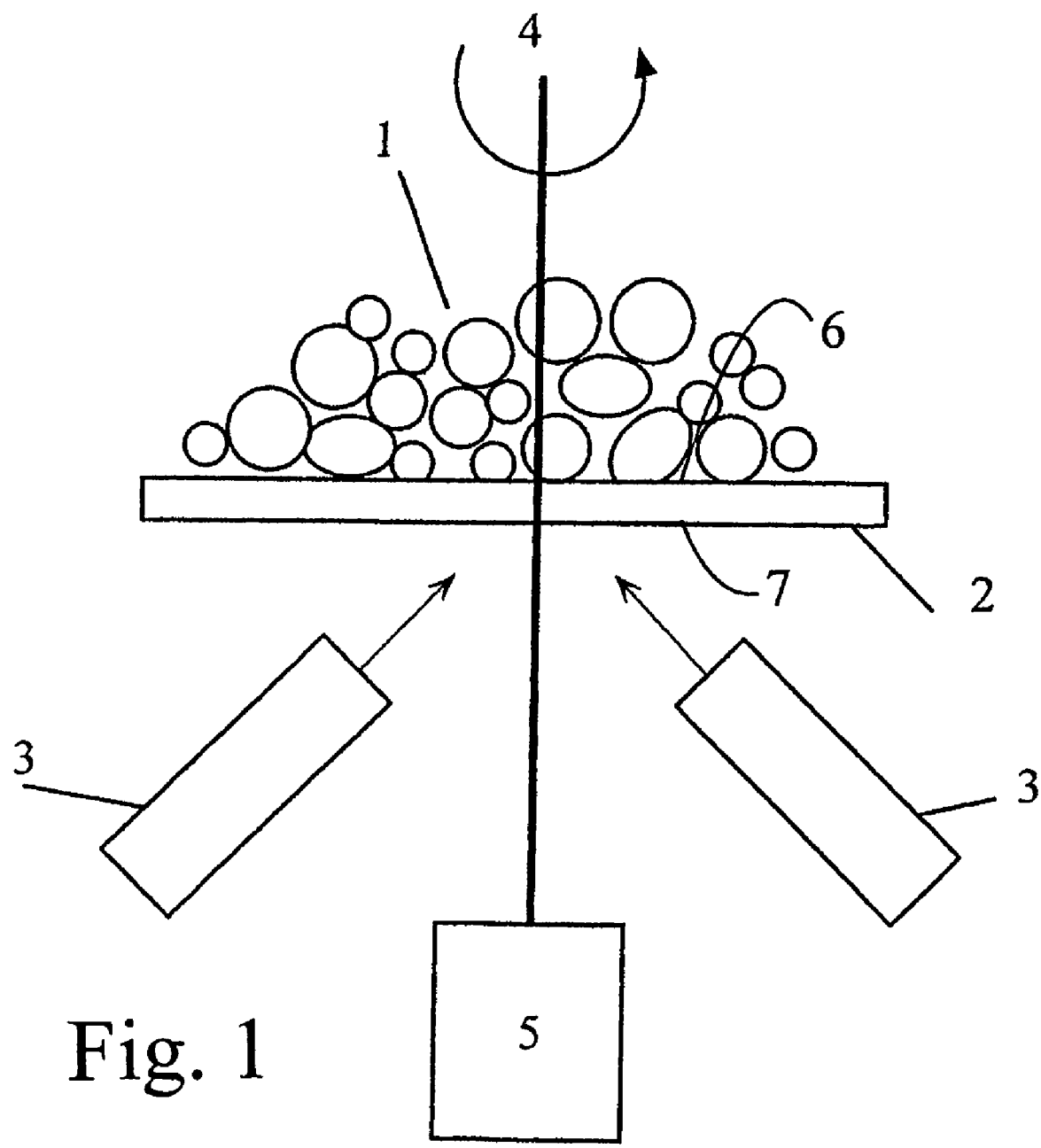

MEASURING METHOD AND SYSTEM FOR MEASURING PARTICLE SIZE AND SHAPE OF POWDERY OR GRAIN LIKE PARTICLES

BACKGROUND OF THE INVENTION

1. Field of Invention

The present invention relates to a measuring method, according to the preamble of claim 1, for measuring the particle size and shape distribution of powder material. By means of the method, a surface is formed in a controlled manner of the powder material, which can be imaged in precisely controlled exposure conditions.

2. Description of Related Art

FI patent 20000493 discloses an analysis method for a moving granular material. The method is not suitable for accurate optical grain-size distribution analysis, precisely on account of the movement of the material being studied.

U.S. Pat. No. 5,239,358 discloses a method for removing foreign particles from a powder sample. The central component of the invention is a rotating sample plate. Precisely on account of the rotating plate, the method is not suitable for accurate optical grain-size distribution analysis.

JP publication 10010033 discloses a measuring method for a moving powder substance. In this publication, the light passing through a sample is studied. The measuring method does not appear to be accurate.

U.S. Pat. No. 6,122,042 discloses several methods for optical analysis. In the method, comparison image pairs of a stationary sample are not created.

WO publication 03062804 discloses a method for optical analysis. In the method, the fine-particle distribution is not determined, nor are comparison image pairs created from a stationary sample.

It is also known that the particle-size distribution can be relatively reliably defined from the surface of a powder or granular material (scientific publication: Laitinen, N., Antikainen, O., and Yliruusi, J. (2002) Does a powder surface contain all necessary information for particle size distribution analysis? European Journal of Pharmaceutical Sciences, 17(4-5), 217-227). In this case, the subject of the measurement of particle size is an undispersed powder, from which a level surface is made. Thus the method cannot be used to measure a property of a single particle, but of a larger group of particles.

The determining of a particle distribution from a powder surface, using the prior art, takes place according to the following description. For example, the most level surface possible is made from a powder sample in a sample container. In the method, a light source is used to illuminate the sample surface, in such a way that shadows are formed on the surface. The shadow formation is utilized by converting the surface information of the powder to depict the particle size of the powder material. To illuminate the sample it is possible to use, for example, two light sources placed symmetrically on either side of the sample. The sample is then illuminated by alternating the light sources and taking a digital image using a CCD camera, in such a way as to obtain two digital images. The sample must remain stationary, as first of all the difference is calculated between the two grey-tone matrices from which the digital image is formed. For a theoretically completely even sample, the difference matrix is formed of elementary units that are zero. For a real difference matrix, the elementary units receive values that are integers between −255-+255 (if a grey-tone range of 0-255 is used). The next stage of the calculation determines how many elementary units of the difference matrix have received a certain value of the 511 possible values.

The known measuring method is based on the fact that a sample with a certain grain-size distribution will always form a grey-tone difference distribution that is specific to it. To be able to use the measuring method, a model must be made for the pitch of the actual size distribution of the grain of the grey-tone difference distribution, which will convert the measurement result obtained into a size distribution. In the known method, a PLS (partial least squares) model is used, which is based on principal-component analysis. The independent variables are the 511 values of the distribution of the elementary units of the aforementioned grey-scale matrix while the response variable is the percentage mass fraction on each screen of the screen series of the screen analysis of the grain batch. With the aid of the model in question, it is possible to determine the grain-size distribution, which corresponds to the result obtained by screen analysis of the same powder material. A corresponding model can be similarly calculated for other generally used methods for determining particle size.

In the known method, stable collimated (parallel) and direct current light sources are used. The illumination can be arranged using two stable light sources, or using a single light source, the light provided by which is dispersed optically, in such a way as to make it possible to illuminate the sample symmetrically in two directions. A matrix-type (CAD) camera or similar, or generally any opto-electric camera or image-recording method whatever can be used to detect the image signal. Imaging can also be performed using only a single light source, in which case that the sample is rotated. Afterwards, the images can be combined according to the above matrix-difference principle. In the manners described above, it is also possible to take several images of a single sample surface by rotating the sample, or by altering the imaging angle. In this way it is possible to obtain more information from the surface of the powder.

The material being studied can be a surface created in a suitable manner from powder, granular, or other multi-component samples. The surface can be created by wiping with a suitably flat spatula or plate. Repeatability is a problem in the sample preparation method of the aforementioned measurement technique. In the method in question, the powder surface is made by pouring an excess amount of powder into a sample container, after which the excess is removed using a suitable plate, while simultaneously attempting to create a level surface from the powder. The surface is leveled by pulling the levelling plate horizontally over the upper edge of the sample container. When the surface is leveled in this manner, unevenness can form on the surface due to the manufacture of the sample, for example, large particles in the powder can cause wipe traces on the surface. It can also be difficult to level powders with small particles that cohere easily to each other (cohesive powders), when using the levelling method in question. The aforementioned problems will lead to errors in measurement.

BRIEF SUMMARY OF THE INVENTION

The invention disclosed here is intended to eliminate the defects and weaknesses of the prior art described above. With the aid of the invention, a particle-size and shape measuring method based on surface images, which is considerably more accurate, faster, and easier, will become possible. In addition, the use of the invention will provide information on the arrangement and caking of the material being examined. With the aid of the invention it is also easier to automate sample preparation, in which case the material to be analysed can be collected directly from various powder-substance processing processes.

According to the invention, these intentions can be achieved by forming controllably and repeatably a surface from a powder material, which can be imaged under precisely controlled lighting conditions. The controllably manufactured surface is obtained by using a transparent plane surface, through which the powder is imaged, to make the sample. The transparent plane surface can be of plastic, glass, quartz, or some other transparent material. The plane can be in the sample container, which can be closed in a controlled manner and the plane can then be imaged from different directions. The sample container can have several transparent surfaces/planes, through which the sample is imaged. For example, the container can have a cubic shape, in which case there will be several transparent surfaces. There can be sample containers of different sizes, always depending on the properties and amounts of the material being analysed.

The invention thus relates to, among other things, a sample-preparation method, which is utilized by when using a known particle-size measuring technique (Laitinen et al. 2002, see line 11 above), which preferably includes at least the following components:

a light source (one or more preferably direct-current light sources), which illuminate the sample at slanting angle. The sample can be illuminated using these light sources controllably and symmetrically by parallel collimated light, a camera, preferably a digital camera (for example, a CCD camera), in which the image of the subject is focussed through suitable optics, an image-capturing devices, such as a microcomputer, or its image-capturing card, and software for use in calculation.

More specifically, the said method according to the invention is characterized by what is stated in the characterizing portion of Claim 1.

The system according to the invention is, in turn, characterized by what is stated in the characterizing portion of Claim 9.

The use according to the invention is, in turn, characterized by what is stated in the characterizing portion of Claim 16.

In the following, the invention is examined in detail with reference to the accompanying drawings, which show cross-sections of various sample-preparation containers according to the invention.

DETAILED DESCRIPTION OF THE INVENTION

FIG. 1 shows a sample plate 2, on top of which there is a powder sample 1. The sample plate 2 comprises at least two surfaces, a first surface 6 on the side with the sample 1, and an opposite surface to this, the imaging surface 7. When the powder material is poured onto the sample plate 2, it forms a powder surface that is specific to it. In this arrangement, the powder 1 is supported on the first surface 6 of the sample plate 2 and forms an even measuring surface. The powder surface is illuminated in a controlled manner by light sources 3 from the side of the imaging surface 7 and is imaged using a suitable camera 5. In addition, the sample 1 or the camera 5 can be rotated around its optical axis 4.

Figure 2:
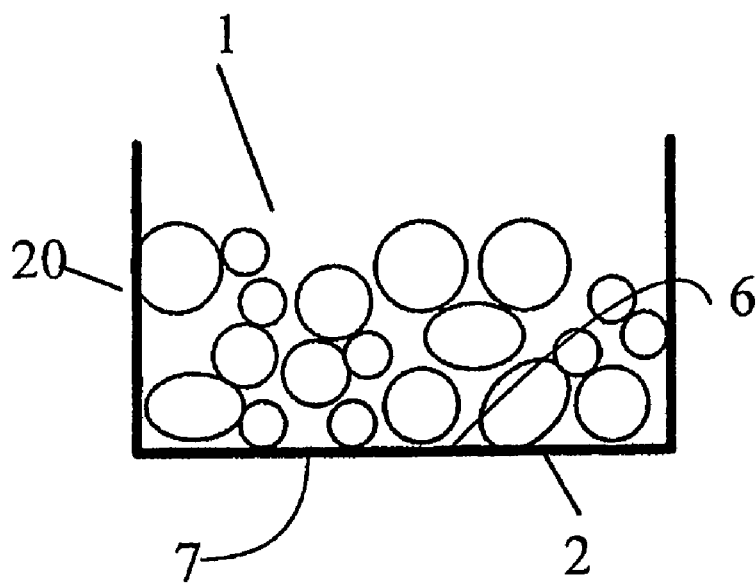

FIG. 2 shows a sample container 20, inside which is a powder sample 1. When a powder material is poured into the container a surface specific to it is formed on the first surface 6 of the plate 2. The surface of the powder can be imaged through the sample plate 2 from below, from the direction of the imaging surface 7.

Figure 3:
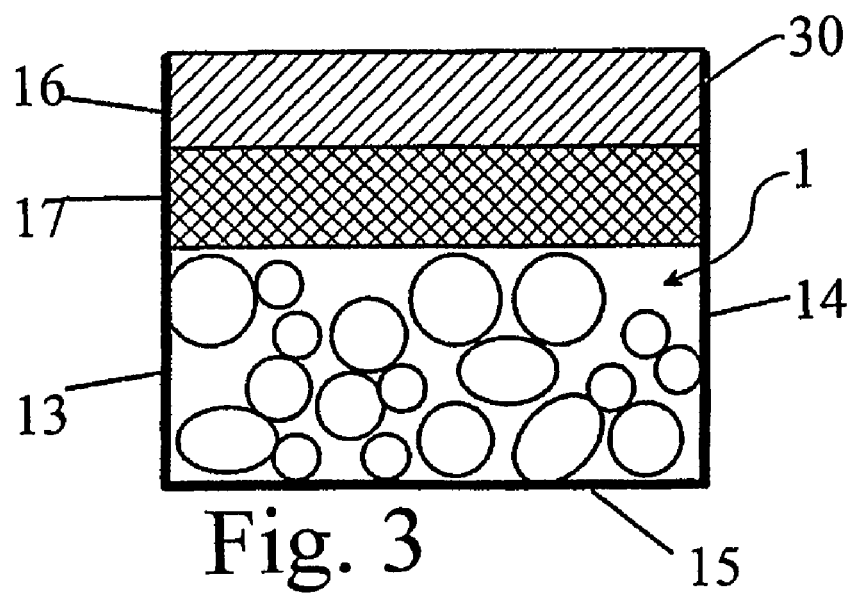

FIG. 3 shows a cross-section of a cubical sample container 30, in which the powder sample can be imaged through transparent planes, the walls 13, 14, and 15. In this way, information on the sample 1 is obtained in the directions of three axes (x,w,z). In the sample container there is also a sealing cover 16 and a plastic seal 17, with the aid of which the sample is made to remain in place and the sample can, for example, be rotated, so that it can be imaged from different directions by a camera. The sealing cover 16 can be, for example, a rubber stopper or some other suitable plug. The plastic seal 17 can be, for example, of cotton wool or some other plastic material. The closing mechanism of the sample container 30 can be equipped with a suitable locking method. The layering, in other words the degree of flow of the fine-grain material component, in the vertical direction of the sample container, of the sample 1 can also be examined through the side surfaces 13 and 14.

Figure 4:
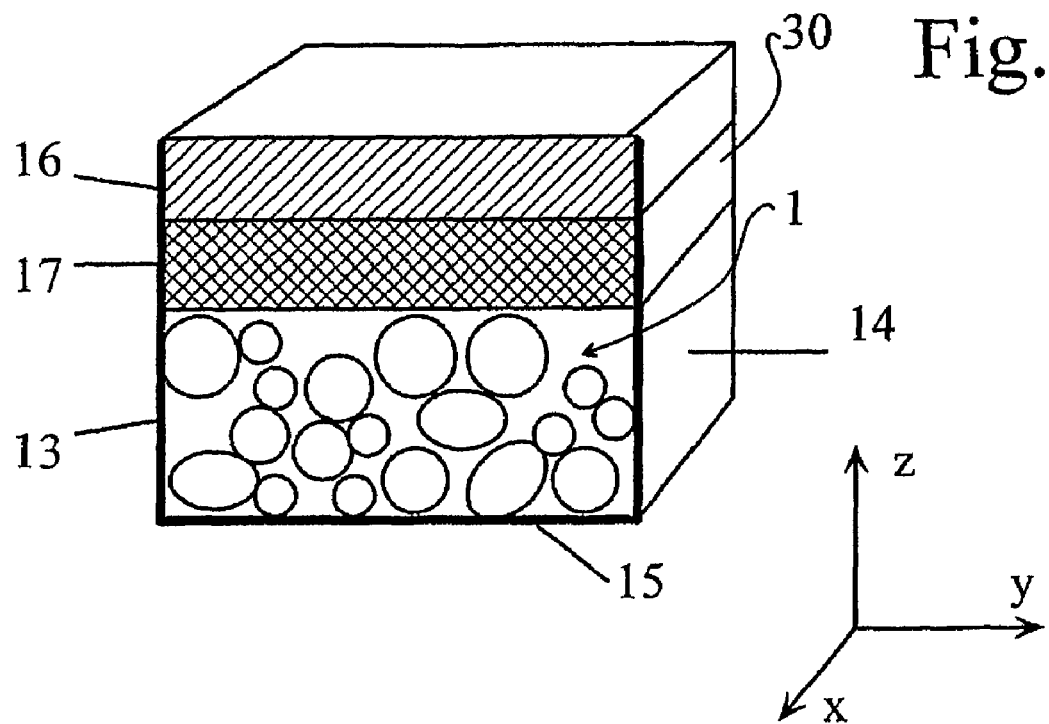

In FIG. 4, the cubical sample container 30 of FIG. 3 is shown in a side view, in which case the powder sample 1 can be imaged through the transparent sample plates 13, 14, and/or 15. In this way information is obtained on the sample 1 in the direction of three axes (x,y,z). In addition, the sample container 30 has a closing mechanism 16 and a damper layer 17, which evens the pressure acting on the sample and with the aid of which the sample 1 is made to remain in place and the sample can be, for example, rotated, so that it can be imaged from different directions by a camera.

Figure 5:
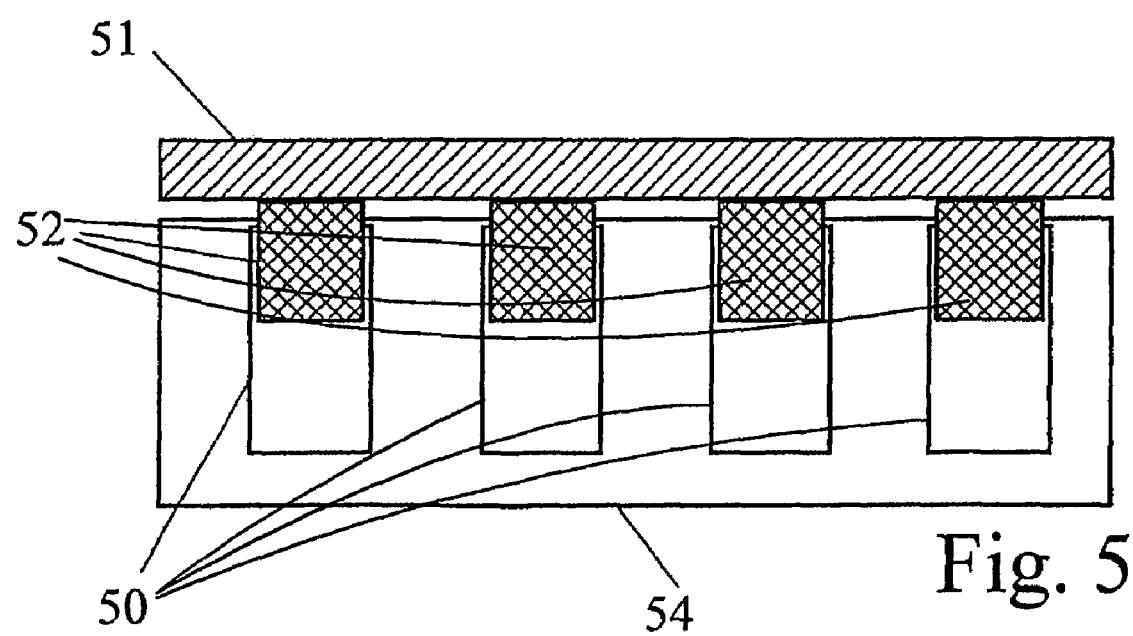

The sample container can also be multi-chambered according to FIG. 5, so that the sample is simultaneously in several containers 50 in the frame 54. The closing mechanism 51 of the sample container is unified and also includes sample-chamber-specific damping stopper pieces 52.

Figure 6:
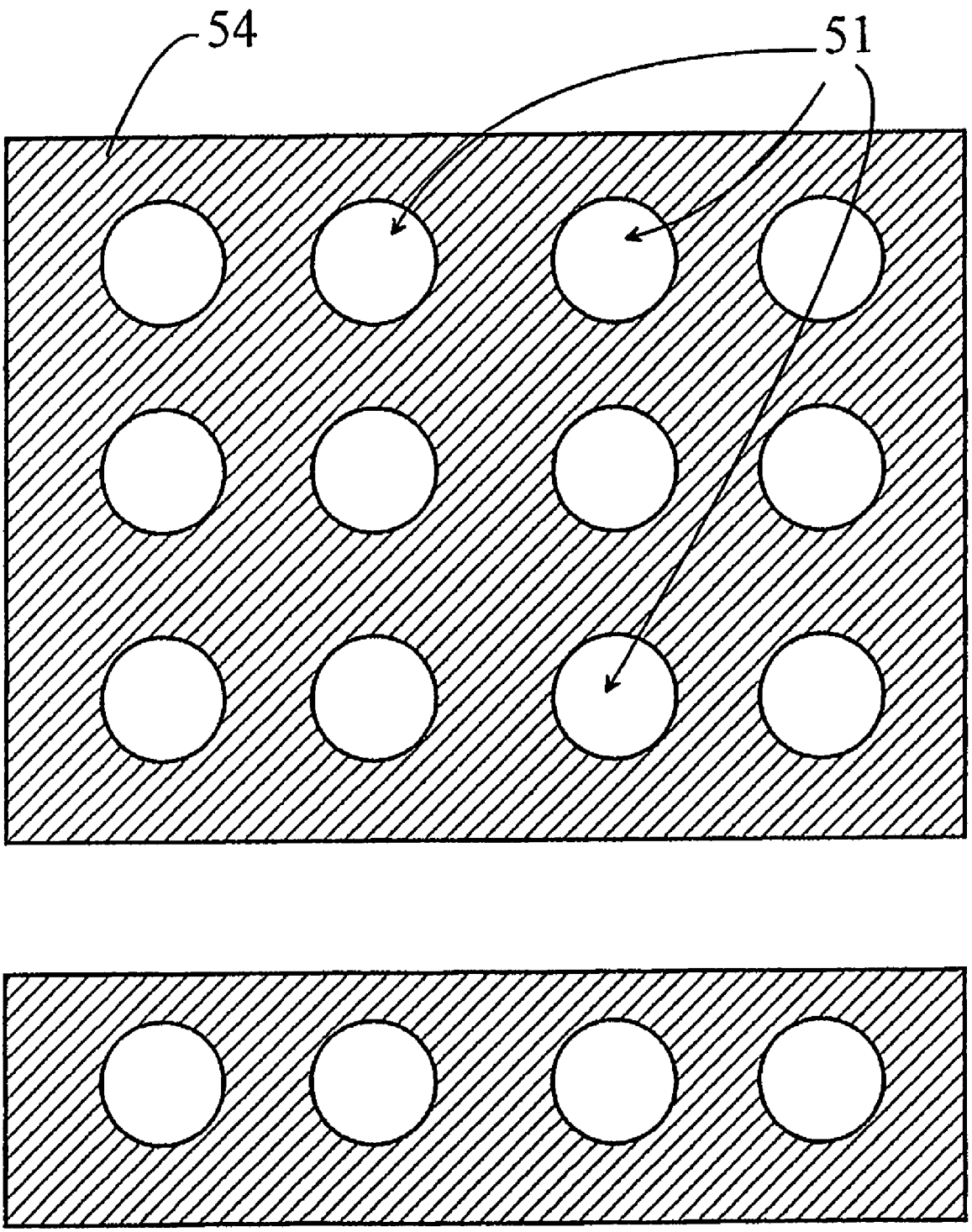

FIG. 6 shows a top view of the frame component 54 of FIG. 5, showing the possible annular openings of the sample chambers 50. The sample chambers can thus be set in a flat arrangement, or they can form a long band. Sample-chamber methods of this kind can be utilized to increase the speed of the analysis.

Figure 7:
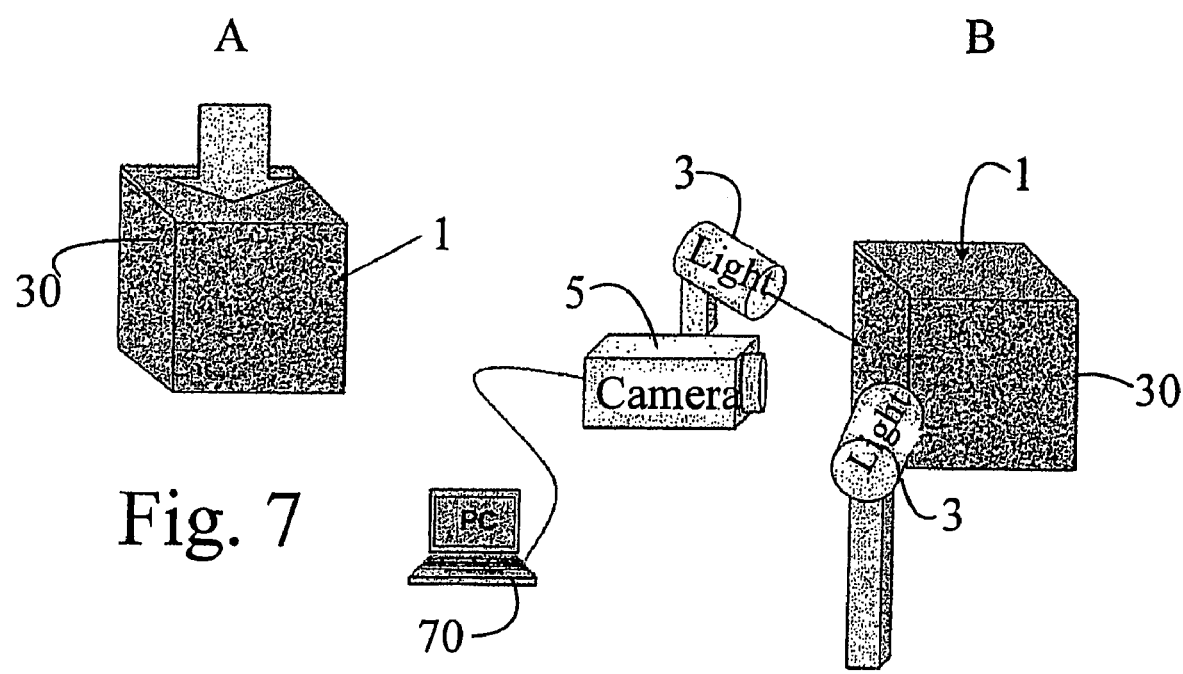

FIG. 7 shows further the entire system, in which, in stage A, a powder sample is poured, for example, into the sample container 30 shown in FIG. 3, either manually or automatically with the aid of dosing devices. In stage B, the sample is illuminated from two directions by light sources 3 and imaged by a camera 5. The camera 5 is connected to a computer 70, in which the interface to the camera 5 is, for example, an image-capture card, or some other similar interface, for example, a USB bus (Universal Serial Bus), and suitable software. The computer 70 can be any computer freely available on the market, such as a desktop or portable computer.

The transparent sample plates are typically in either a vertical or horizontal position, but the plate can naturally also be at a slant, provided the sample rests on the plate. Slanting can typically be implemented in the form of a funnel-like sample container, in which case the sample 1 will rest on a slanting plate. Within the scope of the invention, the slant of the plate can be in the range 0-90°, in which 0° refers to a horizontal surface and 90° to a vertical surface. The sample plate can also be curved, for instance convex or concave, in which case the shape must be taken into account in modelling. The sample plate need not necessarily be of uniform thickness, though uniform thickness will facilitate modelling. In principle, lens-like sample plates are also suitable for the solution according to the invention.

In this publication, the term imaging the sample refers to recording the surface-structure information of the sample. This takes place typically with the aid of a digital camera, but the use of a conventional camera too will permit the use of the method according to the invention. In that case, the information contained in the film material will have to be converted to a numerical form. In this connection, imaging also refers to the creation of surface-structure information, for example, using laser scanning.

The method according to the invention is also suitable for measuring segregation, provided a suitable device is used to cause a controlled vibration of the sample. Known coarseness parameters can then be calculated from the image information.

It is also possible to take only a single image of the sample surface and convert it into a grey-tone vector, on the basis of which the particle size can be calculated, in which case a model is first created and then the particle-size distribution is calculated. The independent variable is the distribution of elementary units in the aforementioned grey-tone vector and the response variable the percentage mass fraction on each screen of the screen series of the screen analysis of the grain batch. With the aid of the model in question, it is possible to determine the grain-size distribution, which corresponds to the result obtained by screen analysis of the same powder material. A corresponding model can also be similarly calculated for other generally used methods for determining particle size.

The calculation relating to segregation can also be performed from a single image.

According to the invention, it is not necessary to use the entire image matrix (the entire area of the image taken), if the essential information can be calculated from some part of the image. This applies to the measurement of size, shape, and segregation.

Thus, in addition to the grey-tone difference distribution, it is also possible to calculate the grey-tone vector from a single image.

In the grey-tone difference distribution there can be more than 511 elementary units, depending on the equipment used, i.e. typically the camera.

The invention claimed is:

1. A measuring method for measuring the properties of a powder or granular sample from the surface information of the sample, in which method
 the sample is leveled for the measurement,
 at least two images of the surface of the sample are taken under different illuminations, the surface structure of the sample remaining at least essentially unchanged in the different measurements, and
 the properties of the sample, such as its grain-size distribution, are determined by using calculation to compare the information material of at least two images,
wherein
 the sample is made to be supported on a transparent sample plate and
 an image is taken through this sample plate.

2. The measuring method according to claim 1, wherein the images are taken through an essentially straight sample plate.

3. The measuring method according to claim 1 or 2, wherein the sample is placed in a sample container, in which there are several transparent sample plates.

4. The measuring method according to claim 1, wherein the sample is placed in a sealed and well-supported manner in the sample container, and the sample container is moved during the measurement, in order to create different kinds of lighting conditions in the different images.

5. The measuring method according to claim 1, wherein the sample is placed in a sealed and well-supported manner in the sample container with the aid of damping and stopper pieces.

6. The measuring method according to claim 1, wherein the sample is placed in a multi-chambered sample container.

7. The measuring method according to claim 1, wherein the sample plate is formed from glass or plastic.

8. The measuring method according to claim 1, wherein the segregation in the vertical direction of the sample is assessed through the vertical walls of the sample plate, for example, by vibrating the sample.

9. A measuring system for measuring the properties of a powder or granular sample from the surface information of the sample, which system includes
 imaging devices for taking at least two images of the surface of the sample, in such a way that the surface structure of the sample is at least essentially unchanged in the different measurements, and
 calculation means for comparing by calculation the information material of at least two images, in order to determine the properties of the sample, such as its grain-size distribution,
wherein the system comprises
 a transparent sample plate, on the first surface of which the sample is arranged to be supported, in which case the imaging devices are arranged on the second side of the transparent sample plate to examine the sample from the imaging surface side of the sample plate.

10. The system according to claim 9, wherein the sample plate is essentially straight and of uniform thickness.

11. The system according to claim 9 or 10, wherein the sample is placed in a sample container, in which there are several transparent sample plates.

12. The system according to claim 9, wherein the sample is placed in a sealed and well supported manner in the sample container and the sample container can be moved during the measurement, in order to create different kinds of lighting conditions in different images.

13. The system according to claim 9, wherein the sample container comprises damping and stopper pieces for supporting the sample in the sample container.

14. The system according to claim 9, wherein the sample container is multi-chambered and comprises several sample containers.

15. The system according to claim 9, wherein the sample plate is of glass or plastic.

16. A measuring method for measuring the properties of a powder or granular sample from the surface information of the sample, in which method the sample is leveled for the measurement, at least one image is taken of the surface of the sample the surface structure of the sample remaining at least essentially unchanged in the various measurements, and the properties of the sample such as grain-size distribution are determined at least by processing the information material by calculation, wherein a model is created, the sample is made to be supported on a transparent sample plate and an image is taken through this sample plate, and only a single image is taken of the sample surface and is converted into a grey-tone vector, and on the basis of the grey-tone vector and the model the particle size can be calculated and then the particle-size distribution is calculated.

* * * * *